United States Patent [19]

Kahan

[11] 4,162,323

[45] Jul. 24, 1979

[54] ANTIBIOTIC N-ACETYL-DEHYDRO-THIENAMYCIN

[75] Inventor: Jean S. Kahan, Rahway, N.J.

[73] Assignee: Merck & Co., Inc., Rahway, N.J.

[21] Appl. No.: 788,491

[22] Filed: Apr. 18, 1977

[51] Int. Cl.² .................. C07D 487/04; A61K 31/40
[52] U.S. Cl. ............................... 424/274; 260/326.31
[58] Field of Search .................. 260/326.31; 424/274

[56] References Cited

U.S. PATENT DOCUMENTS 3,950,357   4/1976   Kahan et al. .................. 260/326.31

*Primary Examiner*—Donald G. Daus
*Assistant Examiner*—Mary Lee
*Attorney, Agent, or Firm*—Hesna J. Pfeiffer; James A. Arno; Julian S. Levitt

[57] ABSTRACT

Antibiotic N-acetyl-dehydro-thienamycin is active against both gram-positive and gram-negative bacteria. The antibiotic is produced by growing a species of Streptomyces in suitable fermentation media.

2 Claims, No Drawings

ANTIBIOTIC N-ACETYL-DEHYDRO-THIENAMYCIN

BACKGROUND OF THE INVENTION

The discovery of the remarkable antibiotic properties of penicillin stimulated great interest in this field which has resulted in the finding of many other valuable antibiotic substances such as: streptomycin, bacitracin, chlortetracycline, oxytetracycline and the like. In general, the activity of such antibiotics is confined either to the gram-positive or to the gram-negative bacterial pathogens. Even in those cases where a broader spectrum of antibacterial activity obtains, certain pathogenic species remain either intrinsically insensitive or have acquired resistance over the course of intensive use of the existing antibiotics in the treatment of various diseases.

Accordingly, the deficiencies of the known antibiotics have stimulated further research to find other antibiotics which will be active against a wider range of pathogens as well as resistant strains of particular microorganisms.

SUMMARY OF THE INVENTION

This invention relates to a new antibiotic agent. More particularly, it is concerned with a new antibiotic substance, herein called antibiotic N-acetyl-dehydro-thienamycin. The invention encompasses the antibiotic in dilute forms, as crude concentrates and in pure forms.

It is an object of the present invention to provide a new and useful antibiotic which is highly effective in inhibiting the growth of various gram-negative and gram-positive microorganisms. Another object is to provide a process for the preparation of this novel antibiotic substance by the fermentation of nutrient media with the herein described microorganism. Other objects will be apparent from the detailed description of this invention hereinafter provided.

The novel antibiotic substance of the present invention is produced by growing under controlled conditions the microorganism *Streptomyces cattleya*.

Based upon extensive taxonomic studies, *Streptomyces cattleya*, isolated from a soil sample, has been designated MA-4297 in the culture collection of MERCK & CO., Inc., Rahway, New Jersey. A culture thereof has been placed on permanent deposit with the culture collection of the Northern Regional Research Laboratories, Northern Utilization Research and Development Division, Agricultural Research Service, U.S. Department of Agriculture, Peoria, Illinois, and has been assigned NRRL accession No. 8057.

*Streptomyces cattleya* (NRRL 8057) is known to produce the antibiotic thienamycin. The production, isolation and characteristics of the antibiotic thienamycin as well as the morphological and cultural characteristics of *Streptomyces cattleya* are described in U.S. Pat. No. 3,950,357. Said U.S. Pat. No. 3,950,357 is herein incorporated by reference.

The novel antibiotic of the invention, N-acetyldehydro-thienamycin is produced during the aerobic fermentation of suitable aqueous nutrient media under controlled conditions via the inoculation with the organism, *Streptomyces cattleya*. Aqueous media, such as those employed for the production of other antibiotics are suitable for producing the antibiotic N-acetyl-dehydro-thienamycin. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, rye, cornstarch, corn meal and the like can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobolt, manganese, iron and magnesium.

It should be noted that the media described in the Examples are merely illustrative of the wide variety of media which may be employed, and are not intended to be limitative.

The fermentation is carried out at temperatures ranging from about 20° C. to 37° C.; however, for optimum results it is preferable to conduct the fermentation at temperatures of from about 22° C.–30° C. The pH of the nutrient media suitable for growing the *Streptomyces cattleya* culture and producing the antibiotic N-acetyl-dehydro-thienamycin can vary from about 6.0 to 8.0.

Although the antibiotic N-acetyl-dehydro-thienamycin is produced by both surface and submerged cultures, it is preferred to carry out the fermentation in the submerged state.

A small scale fermentation of the antibiotic is conveniently carried out by inoculating a suitable nutrient medium with the antibiotic-producing culture and, after transfer to a production medium, permitting the fermentation to proceed at a constant temperature of about 25° C. on a shaker for several days.

The fermentation is conducted in a sterilized flask via a one, two, three or four stage seed development. The nutrient medium for the seed stage may be any suitable combination of carbon and nitrogen sources. The seed flask is shaken in a constant temperature chamber at about 28° C. for two days, or until growth is satisfactory, and some of the resulting growth is used to inoculate either a second stage seed or the production medium. Intermediate stage seed flasks, when used, are developed in essentially the same manner; that is, part of the contents of the last seed flask are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 25° C. This method of producing antibiotic N-acetyl-dehydro-thienamycin is particularly suited for the preparation of large quantities of the antibiotic.

PHYSICAL AND CHEMICAL PROPERTIES OF ANTIBIOTIC N-ACETYL-DEHYDRO-THIENAMYCIN

N-acetyl-dehydro-thienamycin has an empirical formula of $C_{13}H_{16}N_2O_5S$. The calculated elemental composition corresponding to this empirical formula is: 49.99% carbon, 5.16% hydrogen, 8.97% nitrogen, 25.61% oxygen and 10.26% sulfur.

The nuclear magnetic resonance (NMR) spectrum of N-acetyl-dehydro-thienamycin at 300 MHz in $D_2O$ reveals the following characteristic signals wherein the chemical shifts are given in parts per million (ppm) relative to the internal standard sodium 2,2-dimethyl-2-silapentane-5-sulfonate (DSS) and coupling constants in Hz:

1.29 (d, J=6, $CH_3$); 2.08

(S, $CH_3C$ );

3.10 (d,d, J=12.5, 8.7, 1H of $CH_2C$);
3.21 (d,d, J=12.5, 9.5, 1H of $CH_2C$);
3.39 (d,d, J=6.0, 2.5, $H_6$);
4.22 (m, $H_5$ and $H_7$);
6.07 (d, J=13.5, HC=);
7.19 (d, J=13.5, HC=).

When the ultraviolet absorption spectrum of N-acetyl-dehydro-thienamycin was measured at pH 7 in aqueous solutions, it revealed a peak at 307.5 nm and a trough at 262 nm.

N-acetyl-dehydro-thienamycin has a molecular structure as follows:

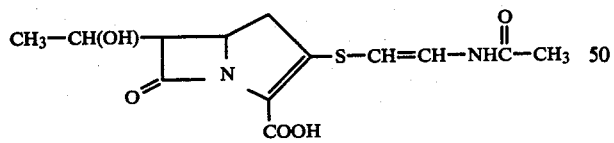

The antibiotic N-acetyl-dehydro-thienamycin is further characterized by the following antibiotic spectrum profile. The test employs the Bauer-Kirby disc diffusion method modified only in respect to the 2 mm. agar depth employed here. The results, expressed in terms of the diameter in millimeters of the zone of inhibition are set forth in Table 1.

TABLE 1

| Organism | | 0.0025 HEAU* /disc |
|---|---|---|
| Staphylococcus aureus | 2985 | 15.5 |
| Staphylococcus aureus | 2314 | 13.0 |
| Escherichia coli | 2884 | 13.0 |
| Escherichia coli | 2891 | 10.5 |
| Enterobacter cloacae | 2646 | 8.5 |

TABLE 1-continued

| Organism | | 0.0025 HEAU* /disc |
|---|---|---|
| Enterobacter cloacae | 2647 | 11.0 |

*HEAU described in section titled "Hydroxylamine-Extinguishable Absorbance Units".

N-acetyl-dehydro-thienamycin is a valuable antibiotic active against various gram-positive and gram-negative bacteria and, accordingly, finds utility in human and veterinary medicine. The compound of this invention can be used as antibacterial drugs for treating infections caused by gram-positive or gram-negative bacteria, for example, against Staphylococcus aureus, Proteus mirabilis, Escherichia coli, Klebsiella pneumoniae, and Enterobacter cloacae. The antibacterial material of the invention may further be utilized as additives to animal feedingstuffs, for preserving foodstuffs and as disinfectants. For example, it may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The antibiotic of this invention may be used in any one of a variety of pharmaceutical preparations as the sole active ingredient or in combination either with one or more other antibiotics or with one or more pharmacologically active substances. As an example of the former, an aminocyclitol antibiotic such as gentamicin may be coadministered in order to minimize any chance that resistant organisms will emerge. As an example of the latter, diphenoxylate and atropine may be combined in dosage forms intended for the therapy of gastroenteritis. The antibiotic may be employed in capsule form or as tablets, powders or liquid solutions or as suspensions or elixirs. It may be administered orally, topically, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In veterinary medicine, such as in the treatment of chickens, cows, sheep, pigs and the like, the composition may, for example, be formulated as an intramammary preparation in either long-acting or quick-release bases.

The dosage to be administered depends to a large extent upon the condition of the subject being treated, the weight of the host and the type of infection, the route and frequency of administration, the parenteral route being preferred for generalized infections and the oral route for intestinal infections.

Included in this invention are the non-toxic, pharmaceutically acceptable salts of N-acetyl-dehydro-thienamycin for example, the pharmacologically acceptable salts formed with inorganic and organic bases; which include, for example, metal salts derived from alkali metal or alkaline earth metal hydroxides, carbonates or bicarbonates such as those derived from sodium, potassium, ammonium and calcium and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, aminopolyamino and guanidino-substituted lower alkanoic acids and nitrogen-containing heterocyclic amines.

In the treatment of bacterial infections in man, the compound of this invention is administered orally or parenterally, in accordance with conventional procedures for antibiotic administration, in an amount of from about 2 to 600 mg./kg./day and preferably about 2 to 50 mg./kg./day in preferably divided dosage; e.g. three to four times a day. They may be administered in dosage units containing, for example, 25, 250, 500 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use; all of such adjustments being within the skill of the practitioner in the field.

The antibiotic containing fermentation broths produced in accordance with the procedures described herein have estimated activities ranging from about 0.1 to 2 $\mu$g. per ml. Antibiotic preparations can be purified and the antibiotic recovered by a number of procedures.

One such procedure comprises extracting acidified (e.g. HCl, $H_2SO_4$, acetic) fermentation broths with ethyl acetate, isobutyl ketone, amyl acetate or similar solvents and back-extracting the isolated solvent phase into an aqueous solution maintained at a pH between 5.5 and 7.5.

Further purification can be achieved by passing such an extract through a column of silica gel particles bearing a bonded hydrocarbon surface, preferably $C_{18}$. If still further purification is desired, the eluate can be passed through a column packed with a polystyrene, non-polar hydrophobic crosslinked divinylbenzene polymer such as XAD-1, 2 and 4, preferably XAD-2 (manufactured by Rohm & Haas, Washington Square, Philadelphia 5, Pa.).

A method of obtaining further purification is to pass the above eluate in 50% methanol through a column containing a strongly basic anion exchange resin. Illustrative of such resins are those having a styrenedivinylbenzene matrix, for example, the polystyrene nuclear quaternary ammonium resin Dowex 1×4 (manufactured by Dow Chemical Co., Midland, Michigan), in the chloride cycle. Other representative members of this class of strongly basic exchange resins include the following: Duolite A-40, A-42, A-101, A-102 and A-114 (manufactured by Chemical Process Co., Redwood City, Calif.); Amberlite IRA-400, IRA-401, and IRA-410 (manufactured by Rohm & Haas, Washington Square, Philadelphia 5, Pa.).

The antibiotic contained in the eluate can be further purified by gel filtration through a polyacrylamide gel having a pore size which excludes molecules having a molecular weight greater than 1800. A preferred gel is Bio-Gel P-2 (manufactured by Bio.Rad, Richmond, Calif.).

A preferred method for recovering pure N-acetyl-dehydro-thienamycin is to extract it from acidified broth using ethyl acetate, back-extract the separated solvent phase with a neutral aqueous solution and pass the aqueous back-extractant through a column of silica gel particles bearing a bonded $C_{18}$ surface. The collected eluate may be further purified by chromatography in 50% methanol on anion exchange resins of the polystyrene-trimethylammonium type (e.g. Dowex 1×4 Cl-400 mesh) and gel permeation resins (e.g. Bio-Gel P-2, 200–400 mesh).

Assays:

Assays of biological activity are run according to the following disc-diffusion method using either *Staphylococcus aureus* ATCC 6538P or *Vibrio percolans* ATCC 8461 as tester organism.

An overnight growth at 37° C. of *Staphylococcus aureus* ATCC 6538P in nutrient broth plus 0.2% yeast extract (NBYE) is diluted with NBYE to a suspension having 40% transmittance at a wavelength of 660 nm. A 33.2-ml. portion of this diluted suspension is added to one liter of NBYE containing 15 g. of agar and maintained at 47°–48° C. Ten-ml. portions of this suspension are poured into petri dishes of 85 mm. diameter and these plates are chilled and held at 4° C. until used (five day maximum).

An overnight growth at 28° C. of *Vibrio percolans* ATCC 8461 in nutrient broth plus 0.2% yeast extract (NBYE) is diluted with NBYE to a suspension having 50% transmittance at 660 nm. A 33.2-ml. portion of this diluted culture is added to one liter of NBYE containing 15 g. of agar maintained at 46° C. Five-ml. portions of this suspension are poured into petri dishes of 85 mm. diameter, and these plates are chilled and held at 4° C. until used (five day maximum).

Samples of antibiotic to be assayed are diluted to an appropriate concentration and applied to ¼ inch (6.25 mm.) or ½ inch (12.5 mm.) diameter discs, 25 μl. being applied to a ¼ inch (6.25 mm.) disc. and 100 μl. being applied to a ½ inch (12.5 mm.) disc. Discs are placed on the surface of the assay plate. *Staphylococcus aureus* plates are incubated at 37° C. overnight; *Vibrio percolans* plates are incubated at 28° C. overnight. The zone of inhibition is measured as mm. diameter and determines antibiotic content.

Hydroxylamine-Extinguishable Absorbance Units (HEAU)

The proportion of absorbance measured near or at the UV absorption maxiumum which can be attributed to the antibiotic content of samples is determined by the selective extinction of this absorbance (with concommitant inactivation of antibiotic activity) upon reaction with dilute hydroxylamine.

Freshly prepared, neutralized hydroxylamine ($NH_2OH.HCl$ plus NaOH to a final pH of 7) is added to unbuffered samples of antibiotic to be tested; in the case of well-buffered neutral pH solutions, unneutralized $NH_2OH.HCl$ is used. Hydroxylamine is added to a final concentration of 10 mM and the reaction is allowed to progress at room temeprature for at least 30 minutes. The resulting absorption in the reacted sample when subtracted from that of an unreacted sample (after correction for dilution by added reagent) yields the hydroxylamine-extinguishable absorbance. One HEAU of antibiotic when present in one ml., has a hydroxylamine-extinguishable absorbance of 1.0.

The following examples illustrate the methods by which the products of this invention may be obtained. The examples are for illustrative purposes only and should not be taken as limiting the scope of this invention in any manner.

EXAMPLE 1

A tube of lyophilized culture of *Streptomyces cattleya* MA-4297 is opened aseptically and the contents suspended in a 250-ml. baffled, Erlenmeyer flask containing 50 ml. of sterile Medium A having the following composition:

| Medium A | |
|---|---|
| Yeast Autolysate | 10.0 g. |
| Glucose | 10.0 g. |
| Phosphate Buffer* | 2.0 ml. |
| $MgSO_4 \cdot 7H_2O$ | 0.05 g. |
| $CaCO_3$** | 2.0 g. |
| Distilled $H_2O$ | 1000 ml. |
| pH adjusted to 6.5 using NaOH | |
| *Phosphate Buffer Solution: | |
| $KH_2PO_4$ | 91.0 g. |
| $Na_2HPO_4$ | 95.0 g. |
| Distilled $H_2O$ | 1000 ml. |
| **added after pH adjustment. | |

The innoculated flask is shaken at 28° C. at 220 rpm (2-inch throw) for 30 hours. Forty (40) ml. of the above 30-hour broth is removed aseptically and mixed with 40 ml. of sterile 20% (v/v) glycerol. Two-ml. quantities of the glycerol mixture are pipetted into sterile one-dram vials which are then frozen and stored in the vapor phase of a liquid nitrogen freezer.

The contents of a frozen vial are used to inoculate a 250-ml. baffled Erlenmeyer flask containing 50 ml. of Medium B having the following composition:

| Medium B | |
|---|---|
| Yeast Autolysate | 10.0 g. |
| Glucose | 10.0 g. |
| Phosphate Buffer* | 2.0 ml. |
| $MgSO_4 \cdot 7H_2O$ | 0.05 g. |
| Distilled $H_2O$ | 1000 ml. |
| pH adjusted to 6.5 using NaOH | |
| *Phosphate Buffer Solution: | |
| $KH_2PO_4$ | 91.0 g. |
| $Na_2HPO_4$ | 95.0 g. |
| Distilled $H_2O$ | 1000 ml. |

This seed flask is shaken at 28° C. at 220 rpm (2-inch throw) for 48 hours. Aliquots of 0.8 ml. of this seed flask are used to inoculate six baffled, 250-ml. Erlenmeyer flasks containing 40 ml. of Medium B having the same composition as the above Medium B. These six baffled, 250-ml. Erlenmeyer flasks are shaken at 28° C. at 220 rpm (2-inch throw) for 24 hours. Forty ml. of 20% (v/v) sterile glycerol are added to each flask. Aliquots of 2.5 ml. of the resulting mixtures are pipetted into sterile one-dram vials, labeled to identify them and stored at −87° C.

One of the above frozen labelled vials is thawed at 37° C. and 1 ml. of the contents used to inoculate a 250-ml. baffled Erlenmeyer flask containing 40 ml. of Medium C having the following composition:

| Medium C | |
|---|---|
| Sucrose | 30.0 g. |
| Distiller's Solubles | 15.0 g. |
| Yeast Extract | 5.0 g. |
| Distilled $H_2O$ | 1000 ml. |
| pH adjusted to 7.3 using NaOH | |

This seed flask is shaken at 28° C. at 220 rpm (2-inch throw) for 48 hours. One-ml. portions from this seed flask are used to inoculate four 250-ml., baffled Erlenmeyer flasks containing 40 ml. of the above Medium C composition. These four second stage seed flasks are shaken at 28° C. at 220 rpm (2-inch throw) for 24 hours.

Eight-ml. portions from these second stage seed flasks are used to inoculate 12 two-liter Erlenmeyer flasks containing 160 ml. of Medium D having the following composition:

| Medium D | |
|---|---|
| Glycerol | 15.0 g. |
| Corn Steep Liquor | 15.0 g. |
| Poultry Meal | 10.0 g. |
| Distiller's Solubles | 15.0 g. |
| $CoCl_2 \cdot 6H_2O$ | 0.01 g. |
| $CaCO_3$ | 3.0 g. |
| Polyglycol 2000 | 0.25% by vol. |
| Distilled $H_2O$ | 1000 ml. |
| pH adjusted to 7.5 using NaOH | |

These production flasks are shaken at 25° C. at 150 rpm (2-inch throw) for five days.

One-ml. portions of the second stage Medium C seed flasks are used to inoculate two 250-ml., baffled Erlenmeyer flasks containing 40 ml. of the above-described Medium C. These third stage seed flasks are shaken at 28° C. at 220 rpm (2-inch throw) for 24 hours.

Eight-ml. portions from these third seed flasks are used to inoculate seven two-liter Erlenmeyer flasks containing 160 ml. of Medium D as described above. These production flasks are shaken at 25° C. at 150 rpm (2-inch throw) for four days.

The broths of eight flasks of the five-day fermentation are combined and the pH is 6.75. The combined broths are chilled to 5°–10° C. and centrifuged 15 minutes at 6000 rpm. The supernatant is filtered with the aid of Super-Cel and the filtrate held at 0° C.

The broths of six flasks of the four-day fermentation are combined and the pH is 6.35. These combined broths are chilled to 5°–10° C. and centrifuged 15 minutes at 6000 rpm. The supernatant is filtered with the aid of Super-Cel. Seven-hundred eighty (780) ml. of the filtered four-day fermentation broth are combined with 966 ml. of the filtered five-day fermentation broth. The combined filtrate is divided into seven portions of 250 ml., and each is adjusted to pH 2.5 with 2.5N HCl and extracted at 5° C. with 250 ml. ethyl acetate. The ethyl acetate phase is separated and back-extracted with 6.65 ml. 0.1M MES [2-(N-morpholino)ethanesulfonic acid], pH 7, supplemented with an amount of 2.5N NaOH sufficient to bring the pH of the aqueous back-extract to pH 6.8–7.2. The aqueous back-extract is separated, and remaining traces of ethyl acetate removed by passing a stream of nitrogen over the surface.

The pooled back-extracts have a total volume of 42.5 ml., a pH of 7.03, and contain 12.75 HEAU measured at 307 nm.

The pooled back-extracts are concentrated by rotoevaporation to 7.65 ml. A 0.1-ml. portion is removed for assay and the remainder applied to a liquid chromatographic system prepared as follows:

Two, 1" × 36" stainless steel columns packed with Bondapak $C_{18}$/Porasil B ®, 37–75 micron particle size range, are coupled in series via a six-inch length of 0.03-inch stainless steel tubing. The columns are immersed in a water jacket, and water heated to 40° C. is circulated continuously through the jacket. The column is equilibrated prior to use with 0.01M potassium phosphate buffer, pH 5.6: acetonitrile, 95:5 (v/v). The sample is applied using an Altex Scientific, Inc. Model 202-00 rotary injection valve fitted with a 10-ml. loop of teflon tubing.

The column is developed with the above buffer at the rate of 8 ml. per three minutes and monitored at 307 nm using a Laboratory Data Control Constametric II ® Ultraviolet Absorbance Monitor fitted with a 1-cm. pathlength flowcell. Fractions of 8 ml. are collected and a 20-μl. portion of 0.1M $K_2PO_4$ is added to each fraction. The fractions are chilled to 0° C. and assayed for biological activity on *Staphylococcus aureus* assay plates.

N-acetyl-dehydro-thienamycin activity emerges between 624 ml. and 688 ml. of eluate. These fractions are combined, adjusted to pH 6.85 with 2.5N NaOH and are found to contain 9.2 HEAU measured at 307 nm. The pooled fractions are concentrated by rotoevaporation to 1 ml. which is applied to a 1.3 cm. × 8 cm. column of pre-washed XAD-2. The XAD-2 is pre-washed, column-wise, successively with four column volumes: (1) 0.001M EDTA; (2) 1N NaOH; (3) deionized $H_2O$; (4) 1N HCl; (5) deionized $H_2O$; (6) methanol; (7) acetone; and (8) deionized $H_2O$. After the sample is applied, it is followed by 1 ml. of distilled $H_2O$ before the column is developed with distilled $H_2O$. Fractions 1–5 contain 5.56 ml.; remaining fractions are 1-ml. collected at approximately 1 ml./min. The fractions are assayed for biological activity on *Vibrio percolans* assay plates. The majority of N-acetyl-dehydro-thienamycin is located in fractions 9–30. These fractions contain 2.57 HEAU measured at 307 nm.

EXAMPLE 2

A frozen MA-4297 vial labeled to identify containing *Streptomyces cattleya* prepared according to Example 1 to thawed at 37° C. and 1 ml. of the contents used to inoculate a 250-ml. baffled Erlenmeyer flask containing 40 ml. of Medium C having the following composition:

| Medium C: | |
|---|---|
| Sucrose | 30.0 g. |
| Distiller's Solubles | 15.0 g. |
| Yeast Extract | 5.0 g. |
| Distilled $H_2O$ | 1000 ml. |
| pH adjusted to 7.3 using NaOH | |

This seed flask is shaken at 28° C. at 220 rpm (2-inch throw) for 48 hours. One-ml. portions from this seed flask are used to inoculate five 250-ml. baffled Erlenmeyer flasks containing 40 ml. of the above-described Medium C. These seed flasks are shaken at 28° C. at 220 rpm (2-inch throw) for 24 hours. Eight-ml. portions from these 24-hour seed flasks are used to inoculate sixteen two-liter Erlenmeyer flasks containing 160 ml. of Medium D having the following composition:

| Medium D- | |
|---|---|
| Glycerol | 15.0 g. |
| Corn Steep Liquor | 15.0 g. |
| Poultry Meal | 10.0 g. |
| Distiller's Solubles | 15.0 g. |
| $CoCl_2 \cdot 6H_2O$ | 0.01 g. |
| $CaCO_3$ | 3.0 g. |
| Polyglycol 2000 | 0.25% by vol. |
| Distilled $H_2O$ | 1000 ml. |
| pH adjusted to 7.5 using NaOH | |

These production flasks are incubated at 25° C. at 150 rpm (2-inch throw) for five days.

The broths from the 16 production flasks are combined, chilled to 5°–10° C., and centrifuged 15 minutes at 6000 rpm. The supernatant is removed and filtered with the aid of Super-Cel. The filtered broth is divided into 250-ml. portions each of which is adjusted to pH 2.5 with 2.5N HCl and extracted at 5° C. with two successive 250-ml. portions of ethyl acetate. Each ethyl acetate phase is back-extracted with 6.65 ml. 0.1M MES, pH 7 plus enough 2.5N NaOH (approximately 0.3 ml.) to bring the pH of the aqueous back-extract to pH 6.8–7.2. The aqueous back-extracts derived from the first extraction of each portion of broth with ethyl acetate are labeled "first extracts"; those derived from the second solvent extraction are labeled "second extracts". Residual ethyl acetate in the extracts is removed by passing a stream of nitrogen over the liquid surface. The "first extracts" are combined with a resulting volume of 67 ml., pH of 7.05, and a total of 45.6 HEAU measured at 307 nm. The "second extracts" are combined with a resulting volume of 62 ml. pH of 7.05, and a total of 23.6 HEAU measured at 307 nm.

The combined "first extracts" are concentrated by rotoevaporation to 7 ml. A 50-μl. portion is removed for assay, and the remaining 6.95 ml. applied to the liquid chromatographic Bondapak $C_{18}$/Porasil B ® system described in Example 1. The column is equilibrated prior to use with 0.01M potassium phosphate buffer, pH 5.6: acetonitrile, 95:5 (v/v), and the column developed with the same buffer.

Fractions of 10.5 ml. are collected every three minutes until 640 ml. of eluate is collected at which time 5.25 ml. fractions are collected every 1.5 minutes. A 20-μl. portion of 0.1M $K_2HPO_4$ is added to each fraction, and the fractions are chilled to 0° C. and assayed for biological activity on *Staphylococcus aureus* assay plates. The majority of N-acetyl-dehydro-thienamcyin is contained in elution volume 597–655 ml. These fractions are pooled, adjusted to pH 7 with 2.5N NaOH and held at 0° C.

The combined "second extracts" are concentrated by rotoevaporation to 6.3 ml. A 50-μl. portion is removed for assay and the remaining 6.25 ml. applied to the liquid chromatographic Bondapak $C_{18}$/Porasil B ® system described in Example 1. The column is equilibrated prior to use with 0.01M potassium phosphate buffer, pH 5.6: acetonitrile, 95:5 (v/v), and the column developed with the same buffer.

Fractions of approximately 9 ml. are collected every three minutes. A 20-μl. portion of 0.1M $K_2HPO_4$ is added to each fraction and the fractions are chilled to 0° C. and assayed for biological activity on *Staphylococcus aureus* assay plates. The active fractions which demonstrated N-acetyl-dehydro-thienamycin activity are combined and adjusted to pH 7 with NaOH. These combined fractions contain 3.74 HEAU measured at 307 nm.

The combined fractions are concentrated by rotoevaporation to 0.5 ml. A 0.5-ml. quantity of methanol is added. The mixture is centrifuged two minutes at 3000 rpm to separate a precipitate that is formed. The precipitate forms a 0.05–0.1 ml. lower phase. The upper phase is removed and applied to an Altex 25 mm. × 100 mm. column packed with Bio-Gel P-2, minus 400 mesh in 50% methanol to a final packed volume of 25 mm. × 75 mm. The sample is applied using an Altex Model 202-00 rotary injection valve fitted with a 3-ml. loop of teflon tubing. The column is developed with 50% methanol at the rate of 3.3 ml./minute and fractions of approximately 0.55 ml. are collected. Fractions are chilled to 0° C. and assayed for biological activity on *Staphylococcus aureus* assay plates. N-acetyl-dehydro-thienamycin activity is found between 65 ml. and 100 ml. of eluate. Fractions between 65 ml. eluate and 67 ml. eluate are combined with fractions between 90 ml. eluate and 100 ml. eluate and concentrated to 3.4 ml. by rotoevaporation. These fractions contain 0.4 HEAU at 307 nm. Bio-Gel fractions between 67 ml. eluate and 90 ml. eluate are combined and concentrated to 11.5 ml. by rotoevaporation. These fractions contain 1.4 HEAU measured at 307 nm.

The two Bio-Gel P-2 fraction pools are combined and added to the N-acetyl-thienamycin pooled fractions from the Bondapak $C_{18}$/Porasil B ® chromatography of the "first extracts". This solution contains 7.89 HEAU measured at 307 nm and has a volume of 68 ml. Sixty-eight (68) ml. of methanol is added and the resulting mixture applied to a prepared Dowex 1×4 Cl⁻, minus 400 mesh column, 1.55 cm. × 21 cm. The column is prepared prior to use as follows—the resin is defined by decanting from water, packed into the column in 50% methanol and then washed with 7–8 column volumes of 0.5M NaCl in 50% methanol followed by 7–8 column volumes of 50% methanol. The 50% methanol solution of N-acetyl-dehydro-thienamycin from above is applied to the column at the rate of 1 ml./minute, followed by 2–3 ml. of 50% methanol. The column is developed at the rate of 1 ml./minute with 0.09M NaCl + 0.005M $NH_4Cl$ + 0.0003M $NH_4OH$ in 50% methanol; pH = 7.5. Fractions of approximately 5 ml. are collected and assayed for biological activity on *Staphylococcus aureus* assay plates. The N-acetyl-dehydrothienamycin is found from elution volume 505 ml. through 607 ml. Elution volume 519 ml. through 579 ml. are combined and contain 4.4 HEAU measured at 307 nm. These fractions are concentrated by rotoevaporation to 0.6 ml. A 0.6-ml. volume of methanol is added and the mixture centrifuged two minutes at 3000 rpm.

The supernatant is removed from the salt pellet. The salt pellet is washed with 0.2 ml. 50% methanol and the mixture centrifuged two minutes at 3000 rpm. This supernatant is added to the first supernatant. This solution, containing 3.2 HEAU measured at 307 nm, is applied to a 1.65 cm. × 37 cm. Bio-Gel P-2, 200–400 mesh column washed prior to use with 5 ml. saturated NaCl in 50% methanol followed by 2–3 column volumes at 50% methanol. The sample is followed by 2–3 ml. of 50% methanol. The column is developed with 50% methanol and fractions of 1.2 ml. are collected every minute. The fractions are monitored for ultraviolet absorption at 300 nm, and one peak between fractions 26 and 41 is observed. Fractions 28–37, having a 307 nm/262 nm ratio of greater than one are combined and 10 μl. of 1M potassium phosphate buffer, pH 7 added. These combined fractions are concentrated by rotoevaporation to approximately 1 ml. prior to lyophilization and contain an estimated 2.28 HEAU measured at 307 nm.

EXAMPLE 3

A tube of lyophilized culture of an isolate of *Streptomyces cattleya* MA-4297 is opened aseptically and the contents suspended in a 250-ml. baffled Erlenmeyer flask containing 50 ml. of Medium B having the following composition:

| Medium B | |
|---|---|
| Yeast Autolysate | 10.0 g. |
| Glucose | 10.0 g. |
| Phosphate Buffer* | 2.0 ml. |
| $MgSO_4 \cdot 7H_2O$ | 0.05 g. |
| Distilled $H_2O$ | 1000 ml. |
| pH adjusted to 6.5 using NaOH | |
| *Phosphate Buffer Solution: | |
| $KH_2PO_4$ | 91.0 g. |
| $Na_2HPO_4$ | 95.0 g. |
| Distilled $H_2O$ | 1000 ml. |

This inoculated flask is shaken at 28° C. at 150 rpm (2-inch throw) for 48 hours. Ten-ml. portions of this seed flask are used to inoculate three 2-liter baffled Erlenmeyer flasks containing 500 ml. of Medium B having the same composition as the above Medium B. These flasks are shaken at 28° C. at 150 rpm (2-inch throw) for 24 hours. The growth from these 2-liter seed flasks is used to inoculate at 756-liter stainless steel fermentor containing 467 liters of Medium E having the following composition:

| Medium E | |
|---|---|
| Glycerol | 10.0 g. |
| Pharmamedia | 5.0 g. |
| Distiller's Solubles | 10.0 g. |
| $CoCl_2 \cdot 6H_2O$ | 0.01 g. |
| $CaCO_3$ | 3.0 g. |
| Polyglycol 2000 | 0.25% by volume |
| Tap Water | 1000 ml. |
| pH adjusted to 7.3 using NaOH | |

This stainless steel tank fermentor is operated at 28° C. using an agitation rate of 130 rpm and an airflow of 10 cubic feet per minute. At 48 hours, 454 liters of this medium are used to inoculate a 5,670-liter stainless steel fermentor containing 4,082 liters of Medium F having the following composition:

| Medium F | |
|---|---|
| Corn Steep Liquor | 15.0 g. |
| Glycerol | 10.0 g. |
| Pharmamedia | 5.0 g. |
| Distiller's Solubles | 10.0 g. |
| $CoCl_2 \cdot 6H_2O$ | 0.01 g. |
| $CaCO_3$ | 3.0 g. |
| Polyglycol 2000 | 0.25% by volume |
| Tap Water | 1000 ml. |
| pH adjusted to 7.3 using NaOH | |

This tank is operated at 25° C. using an agitation rate of 70 rpm and an airflow of 54.3 cubic feet per minute. After 100 hours, a 100-ml. portions is removed, chilled to 5°–10° C. and centrifuged at 6000 rpm for 15 minutes. The supernatant is filtered with the aid of Super-cel. A 25-ml. portion of the filtrate is adjusted to pH 2.2 to 2.4 with 5N HCl and extracted at 5° C. with 25 ml. of ethyl acetate. The ethyl acetate phase is separated and back-extracted with 2.5 ml. of 0.075M potassium phosphate buffer pH 7.0. The aqueous phase containing 925$A_5$ is separated and remaining traces of ethyl acetate is removed by passing a stream of nitrogen over the liquid surface. A half-inch disk containing 100 μl. of back-extract gives a 24.3 mm. zone on a *Staphylococcus aureus* assay plate.

What is claimed is:

1. The compound having the following structure:

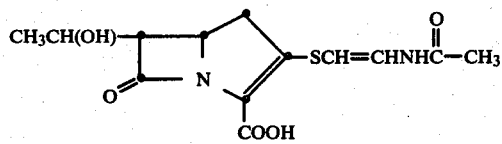

or its pharmaceutically acceptable salts wherein the compound has 300 MHz nuclear magnetic resonance characteristic signals having chemical shifts in ppm as 1.29 (d, J=6, $CH_3$); 2.08

3.10 (d, d, J=12.5, 8.7, 1H of $CH_2C$); 3.21 (d, d, J=12.5, 9.5, 1H of $CH_2C$); 3.39 (d, d, J=6.0, 2.5, $H_6$); 4.22 (m, $H_5$ and $H_7$); 6.07 (d, J=13.5, HC=); 7.19 (d, J=13.5, HC=).

2. A composition comprising an antibacterial effective amount of the compound having the following structure:

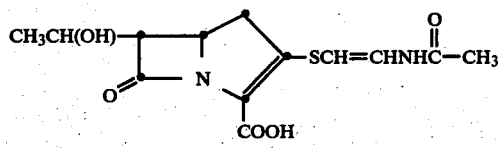

or its pharmaceutically acceptable salts wherein the compound has 300 MHz nuclear magnetic resonance characteristic signals having chemical shifts in ppm as 1.29 (d, J=6, $CH_3$); 2.08

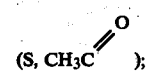

3.10 (d, d, J=12.5, 8.7, 1H of $CH_2C$); 3.21 (d, d, J=12.5, 9.5, 1H of $CH_2C$); 3.39 (d, d, J=6.0, 2.5, $H_6$); 4.22 (m, $H_5$ and $H_7$); 6.07 (d, J=13.5, HC=); 7.19 (d, J=13.5, HC=) and a non-toxic pharmaceutically acceptable carrier therefore.

* * * * *